United States Patent [19]

Go et al.

[11] Patent Number: 5,034,294

[45] Date of Patent: Jul. 23, 1991

[54] ELECTROPHOTOGRAPHIC PHOTOSENSITIVE MEMBER WITH COMPOUND HAVING ELECTRON DONOR AND ACCEPTOR PORTIONS

[75] Inventors: Shintetsu Go; Kazushi Iuchi; Hajime Miyazaki; Hideyuki Takai; Masakazu Matsumoto, all of Yokohama, Japan

[73] Assignee: Canon Kabushiki Kaisha, Tokyo, Japan

[21] Appl. No.: 476,335

[22] Filed: Feb. 7, 1990

[30] Foreign Application Priority Data

Feb. 9, 1989 [JP] Japan ................................. 1-32383

[51] Int. Cl.$^5$ ...................... G03G 5/06; G03G 5/047
[52] U.S. Cl. ......................................... 430/58; 430/59;
430/72; 430/73; 430/75; 430/76; 430/77;
430/78; 430/79; 430/900
[58] Field of Search ...................... 430/58, 59, 72, 73,
430/75, 76, 77, 78, 79, 900

[56] References Cited

U.S. PATENT DOCUMENTS

| | | | |
|---|---|---|---|
| 4,666,809 | 5/1987 | Matsumoto et al. | 430/76 |
| 4,798,777 | 1/1989 | Takiguchi et al. | 430/59 |
| 4,931,371 | 6/1990 | Matsumoto et al. | 430/59 |

FOREIGN PATENT DOCUMENTS

| | | | |
|---|---|---|---|
| 1264954 | 3/1968 | Fed. Rep. of Germany | 430/900 |
| 27705 | 7/1974 | Japan | 430/900 |
| 29465 | 8/1974 | Japan | 430/900 |
| 40935 | 4/1976 | Japan | 430/900 |
| 111249 | 6/1985 | Japan . | |

*Primary Examiner*—Roland Martin
*Attorney, Agent, or Firm*—Fitzpatrick, Cella, Harper & Scinto

[57] ABSTRACT

An electrophotographic photosensitive member has a photosensitive layer on an electroconductive support. The photosensitive layer comprises a compound represented by the general formula (1) or (2) having in the molecule thereof an electron-donating portion and an electron-accepting portion:

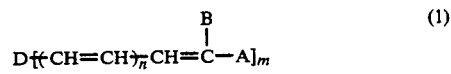

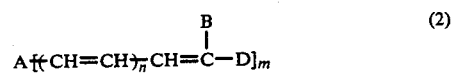

where D is an electron-donating aromatic group or an electron-donating heterocyclic group; A is an electron-accepting aromatic group or an electron-accepting heterocyclic group; B is a hydrogen atom, or an aromatic or heterocyclic group which may form a ring together with A or D; m is an integer of 1, 2 or 3; and n is an integer of 0 or 1.

14 Claims, 1 Drawing Sheet

ELECTROPHOTOGRAPHIC PHOTOSENSITIVE MEMBER WITH COMPOUND HAVING ELECTRON DONOR AND ACCEPTOR PORTIONS

BACKGROUND OF THE INVENTION

1. Field of the Invention

The present invention relates to an electrophotographic photosensitive member. More particularly, the present invention relates to an electrophotographic photosensitive member superior in sensitivity and potential stability.

2. Related Background Art

Recent electrophotographic photosensitive members comprising an organic compound as a main constituent have various advantages such as superior film-forming property, non-pollution, ease of manufacture, and so on, as compared with inorganic type photosensitive members. In particular, some lamination type photosensitive members are practically used which comprises a layer containing a material for generating electric charge on light irradiation (a charge-generating layer) and a layer containing a material for transporting the generated charge (a charge-transporting layer) because of their higher sensitivity and high-charge stability. Photosensitive members employing an azo pigment which is a typical charge-generating material were disclosed in Japanese Patent Application Laid-open No. 59-33445 and No. 60-111249. Such photosensitive members employing the azo pigment as the charge-generating material are not always satisfactory in sensitivity, residual potential, or stability in repreated use, and are limited in the range of selection of the charge-transporting material, thus not satisfying extensive requirement for electrophotographic processes.

SUMMARY OF THE INVENTION

An object of the present invention is to provide an electrophotographic photosensitive member having a high sensitivity and high durability.

Another object of the present invention is to provide an electrophotographic photosensitive member having a sensitivity to light in long wavelength region.

The present invention provides an electrophotographic photosensitive member having a photosensitive layer on an electroconductive support, the photosensitive layer comprising a compound represented by the general formula (1) or (2) having in the molecule thereof an electron-donating portion and an electron-accepting portion:

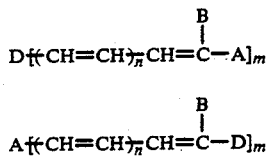

where D is an electron-donating aromatic group or an electron-donating heterocyclic group, A is an electron-accepting aromatic group or an electron-accepting heterocyclic group, B is a hydrogen atom, or an aromatic or heterocyclic group which may form a ring together with A or D, m is an integer of 1, 2, or 3, and n is an integer of 0 or 1.

DETAILED DESCRIPTION OF THE PREFERRED EMBODIMENT

Figure 1:
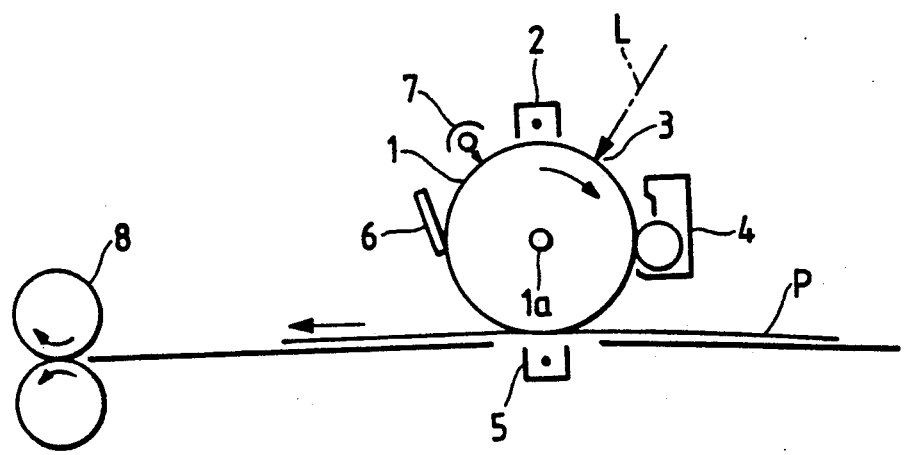
FIG. 1 illustrates an outline of constitution of a usual transfer-type electrophotographic photosensitive member employing a photosensitive member in a drum form.

The electron-donating aromatic group in the present invention includes aromatic monocyclic groups and aromatic condensed polycyclic groups such as benzene, naphthalene, anthracene, phenanthrene, indene, fluorene, etc. which have an electron-donating substituent; assembled ring groups constituted by direct combination through a double bond or the like of two or more of the aforementioned aromatic monocyclic or condensed polycyclic groups; and aromatic amine groups such as triphenylamine, diphenylamine, diphenylmethylamine, etc. which may have an electron-donating substituent.

The electron-donating heterocyclic group includes heterocyclic monocyclic groups such as furan, thiophene, pyrrol, oxazole, thiazole, imidazole, pyridine, pyrazine, acridine, phenazine, benzofuran, benzothiophene, dibenzofuran, dibenzothiophene, benzoxazole, benzothiazole, thianthrene, phenoxazine, phenothiazine, etc. which have an electron-donating substituent; heterocyclic monocyclic groups such as indole, carbazole, iminodibenzyl, tetrathiafulvalene, dibenzotetrathiafulvalene, etc. which may have an electro-donating substituent; condensed heterocyclic groups constituted by condensation with a benzene ring or an aromatic condensed polycyclic group; and assembled ring groups constituted by direct combination through a double bond or the like of two or more of the aforementioned monocyclic or condensed polycyclic groups.

The electron-donating substituent includes alkyl groups such as methyl, ethyl, propyl, butyl, etc.; aryl groups such as phenyl, naphthyl, etc.; aralkyl groups such as benzyl, phenethyl, etc; alkoxy groups such as methoxy, ethoxy, etc.: and substituted amino groups such as dimethylamino, diphenylamino, morpholino, etc.

The electron-accepting aromatic group includes aromatic monocyclic groups and aromatic condensed polycyclic groups such as benzene, naphthalene, anthracene, phenanthrene, indene, fluorene, etc. which have an electron-accepting substituent; assembled ring groups constituted by direct combination through a double bond or the like of two or more of the aforementioned aromatic monocyclic or condensed polycyclic groups; aromatic ketone groups such as benzophenone, fluorenone, benzanthrone, etc. which may have an electron-accepting substituent, and dicyanomethylene derivatives thereof; aromatic thioketone groups; and aromatic quinone groups such as benzoquinone, naphthoquinone, anthraquinone, pyrenequinone, etc. and dicyanomethylene derivatives thereof.

The electron-accepting heterocyclic group includes heterocyclic monocyclic groups such as furan, thiophene, pyrrole, oxazole, thiazole, imidazole, pyridine, pyrazine, acridine, phenazine, benzofuran, benzothiophene, dibenzofuran, dibenzothiophene, benzoxazole, benzothiazole, thianthrene, phenoxazine, phenothiazine, etc. which have an electron-accepting group; condensed heterocyclic groups constituted by condensation with a benzene ring or an aromatic condensed polycyclic group; and assembled ring groups constituted by direct combination through a double bond or the like of two or more of the aforementioned monocyclic or condensed polycyclic groups.

The electron-accepting substituent includes halogen such as fluorine, chlorine, bromine, and iodine; a nitro group; and a cyano group.

In the present invention, the term "electron-donating group" and "electron-accepting group" mean respectively a group having a negative $\sigma$ constant, and a group having a positive $\sigma$ constant of Hammet.

In the general formula (1) and (2), B denotes a hydrogen atom, or an aromatic or heterocyclic group which may form a ring together with A or D. Specifically B may be the same as aforementioned D or A, but preferably hydrogen.

In order to achieve spectrographic sensitivity of electrophotographic photosensitive member in a long wavelength region, the charge-generating material is required to exhibit absorption spectrum at the long wavelength region. Extension of a $\pi$-electron conjugation system, or augmentation of intermolecular interaction are known to give long-wavelength absorption. As to the substituent effect, substituted azobenzenes are reported to have stronger absorption at long wavelength with stronger electron-donating property and with stronger electron-accepting property. This effect is considered to result from the intermolecular charge-transfer interaction through the azo group (—N=N—), namely a $\pi$-electron conjugation chain, of the azobenzene (J. Griffiths, "Colour and Constitution of Organic Molecules", Academic Press London, 1976), and great increase of long wavelength absorption is expected to be given by combination of a strong electron-donating substituent and a strong electron-accepting substituent. However, it is reported that, if the conjugation is interrupted by methylene group (—CH$_2$—) or other non-$\pi$-electron conjugating chain in the azo compound, the absorption spectrum shifts to shorter wavelength (e.g., Konishi, and Kuroki: "Gosei Senryo no Kagaku (Chemistry of Synthetic Dye)" p. 119, Maki Book Co,.)

The compounds of the present invention, which have an electron-donating portion and an electron-accepting portion in a molecule, allow the interaction throughout the entire molecule without interruption of conjugation such as by methylene group (—CH$_2$—).

On the other hand, elevation of charge carrier generation efficiency is required for improving sensitivity in electrophotographic photosensitive members. One factor relating to the charge carrier generation efficiency is a dissociation efficiency of the carrier. A local electric field which is formed by ionically adsorbed gas or the like, is reported to have a great influence on the carrier dissociation efficiency in the case of phthalocyanine compounds (see, for example, Denki Shashin Gakkaishi (Journal of Electrophotographic Society) Vol. 20, p. 216, (1987)). Accordingly, the local electric field generated by charge transfer interaction between the electron-donating material and the electron-accepting material is considered to promote the generation of charge carrier.

As considered above, the compounds of the present invention having an electron-donating portion and an electron-accepting portion in the molecule have achieved remarkably high spectral sensitivity as the result of the remarkable increase in spectral sensitivity at long wavelength and improvement in efficiency of charge carrier generation, which are brought about by the charge transfer interaction between the electron-donating portion and the electron-accepting portion within the molecule through the $\pi$-electron conjugation system and the similar interaction between molecules.

The typical examples of the compounds represented by the general formulas (1) and (2) are shown below.

| Compound No. | Structural formula |
| --- | --- |
| 1 | 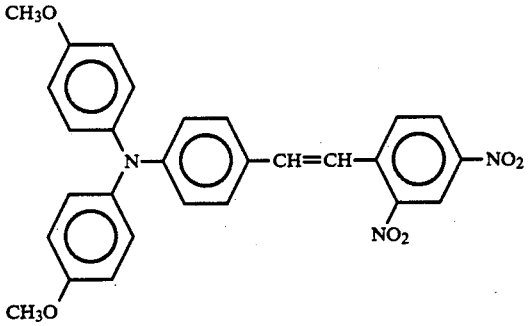 |
| 2 | 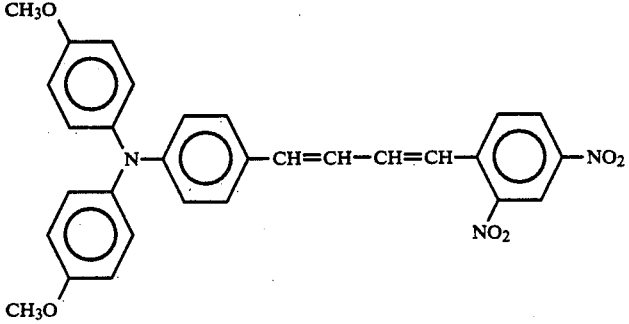 |

-continued

| Compound No. | Structural formula |
|---|---|
| 3 | |
| 4 | |
| 5 | |
| 6 | |
| 7 | |
| 8 | |

| Compound No. | Structural formula |
|---|---|
| 9 | 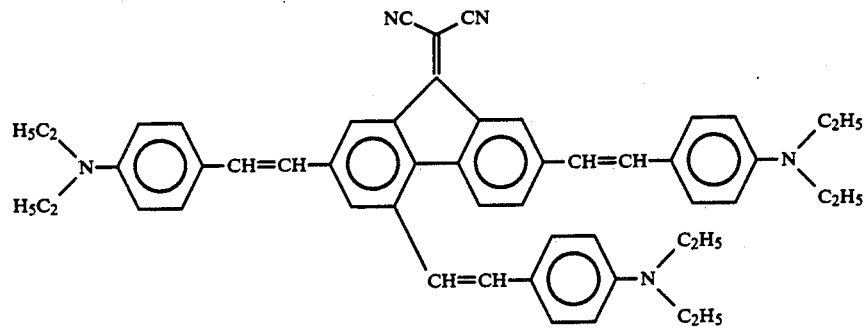 |
| 10 | 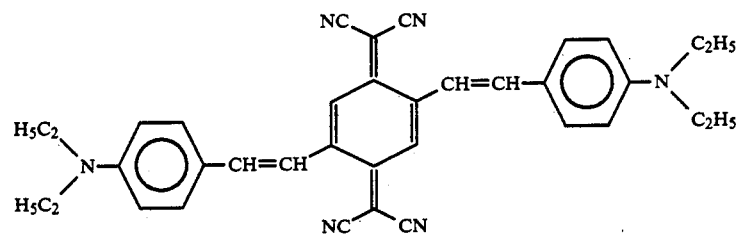 |
| 11 | 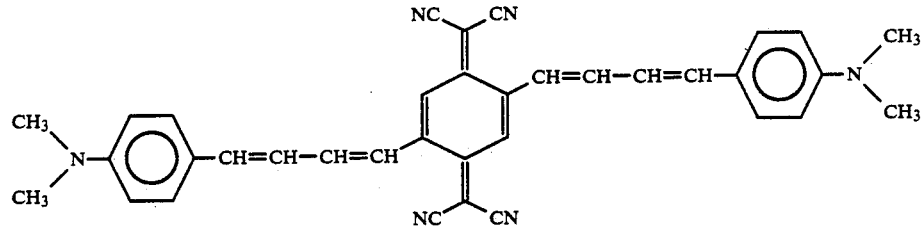 |
| 12 | 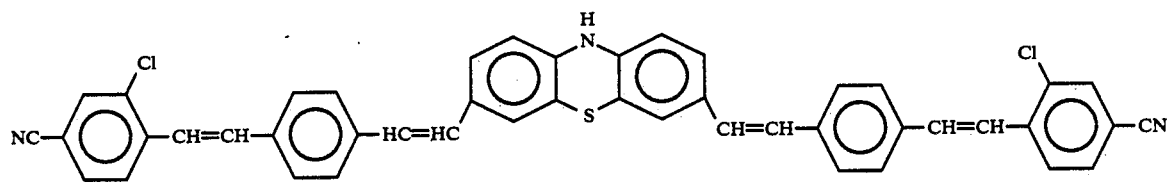 |
| 13 | 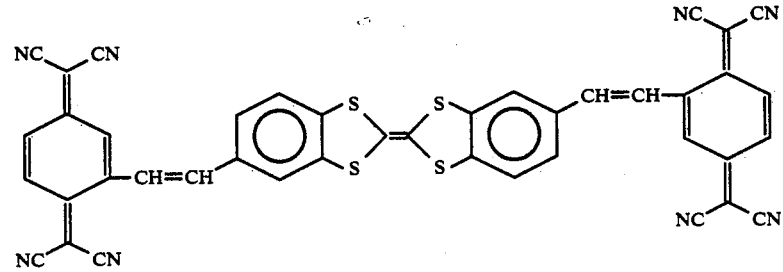 |
| 14 | |

-continued
| Compound No. | Structural formula |
|---|---|
| | 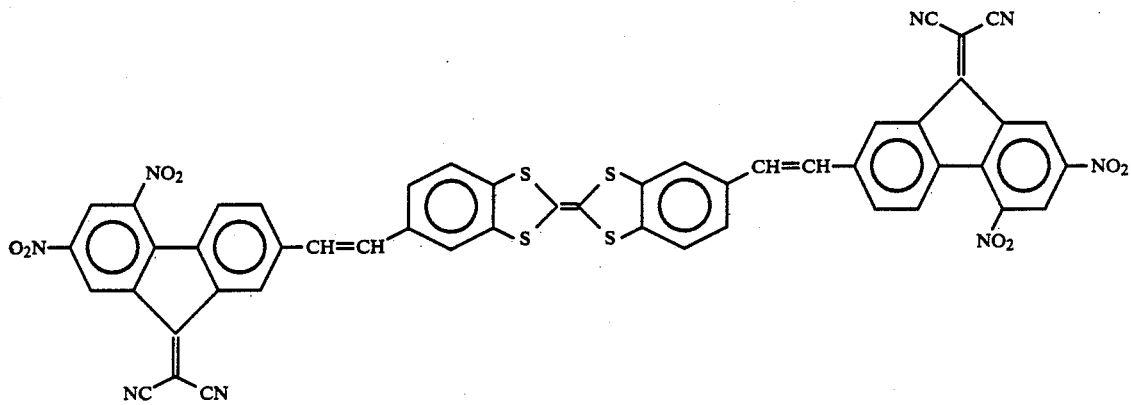 |
| 15 | 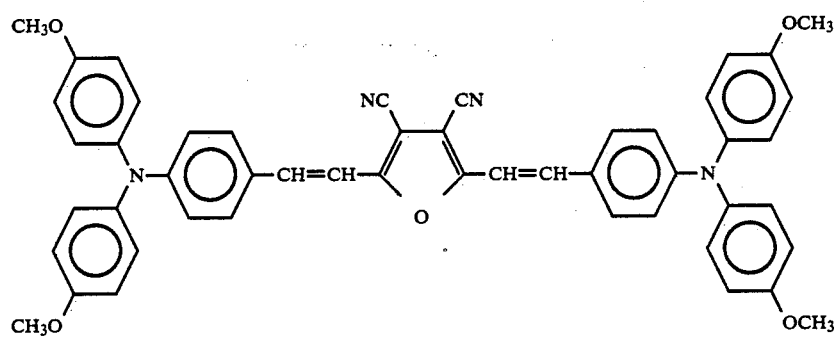 |
| 16 | 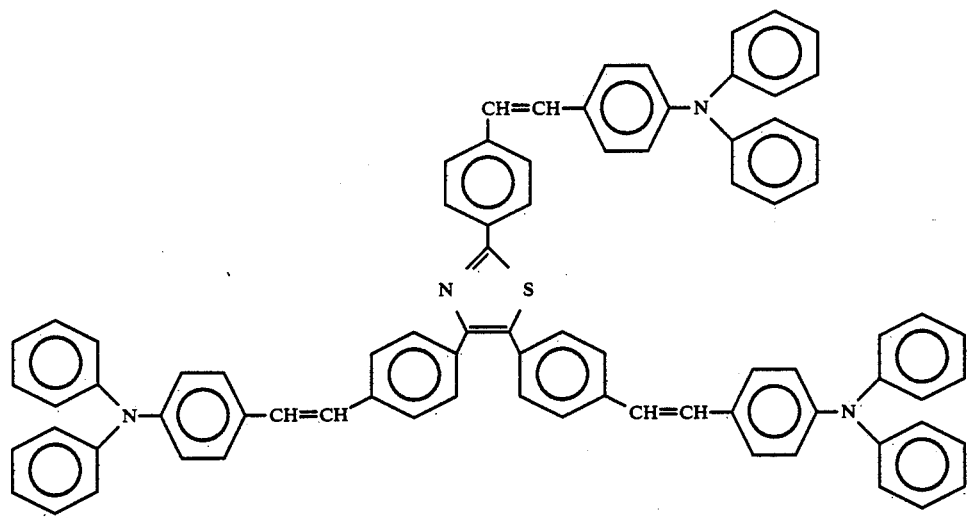 |
| 17 | 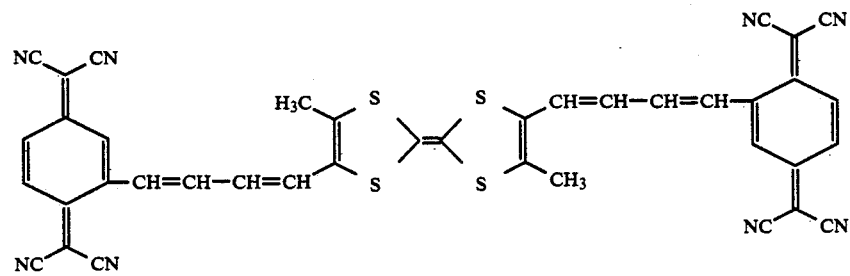 |
| 18 | |

| Compound No. | Structural formula |
|---|---|
|  | 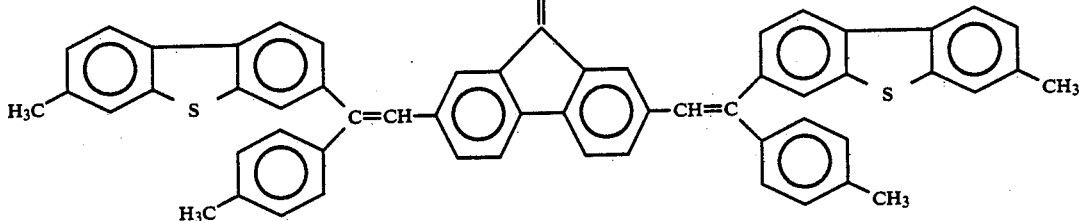 |
| 19 | 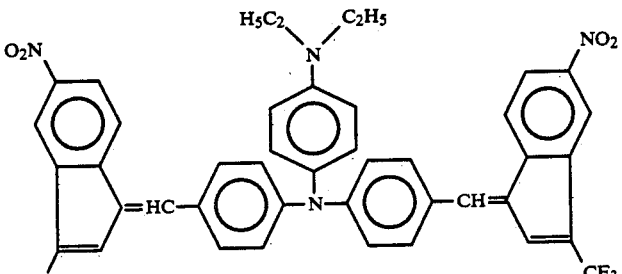 |

The electrophotographic photosensitive member of the present invention has a photosensitive layer containing the compound represented by the general formula (1) or (2) provided on an electroconductive support.

The photosensitive layer may be in any form. A function-separating type of photosensitive layer is particularly preferable which is constituted of a charge-generating layer containing the compound represented by the general formula (1) or (2), and a charge-transporting layer containing a charge-transporting material laminated thereon.

In this case, the charge-generating layer is formed by applying on an electroconductive supporter a coating solution containing a binder resin dispersed in a suitable solvent. The film thickness of the layer is desirably, for example, of 5 μm or less, preferably from 0.01 μm to 1 μm.

The binder resin employed therefor may be selected from a broad range of insulative resins and organic photoconductive resins. The preferable resins include polyvinyl butyrals, polyvinyl benzals, polyarylates, polycarbonates, polyesters, phenoxy resins, cellulose resins, acrylic resins, urethane resins. The content thereof in the charge-generating layer is not more than 80% by weight, preferably notmore than 40% by weight.

The solvent for the binder resin is preferably selected from solvents which dissolve the aforementioned resin but do not dissolve the charge-transporting layer or the subbing layer mentioned below. Specifically the solvent is preferably selected from the group of ethers such as tetrahydrofuran, 1,4-dioxane, etc; ketones such as cyclohexanone, methyl ethyl ketone, etc.; amides such as N,N-dimethylformamide, etc.; esters such as methyl acetate, ethyl acetate, etc.; aromatic solvents such as toluene, xylene, monochlorobenzene, etc.; alcohols such as methanol, ethanol, 2-propanol, etc.; and aliphatic halogenated hydrocarbons such as chloroform, methylene chloride, etc.

The charge-transporting layer which is laminated on the upper side or the lower side of the charge-generating layer, functions to receive charge carriers from the charge-generating layer in an electric field, and transport the carriers to the surface. The charge-transporting layer is formed by applying a charge transporting material, with a suitable binder resin, if necessary, dissolved in a solvent. Generally the thickness of the film is preferably in the range of from 5 μm to 40 μm, more preferably from 15 μm to 30 μm.

The charge-transporting material includes electron-transporting materials and positive-hole-transporting materials. Examples of the electron-transporting materials are electron-attracting materials such as 2,4,7-trinitrofluorenone, 2,4,5,7-tetranitrofluorenone, chloranil, tetracyanoquinodimethane, etc. and polymerized products of these electron-attracting materials.

The examples of the positive-hole-transporting materials are aromatic polycyclic compounds such as pyrene, anthracenne, etc.; heterocyclic compounds such as carbazole, indole, imidazole, oxazole, thiazole, oxadiazole, pyrazole, pyrazoline, thiadiazole, triazole, etc.; hydrazone compounds such as p-diethylaminobenzaldehyde-N,N-diphenylhydrazone, N,N-diphenylhydrazino-3-methylidene-9-ethylcarbazole, etc.; styryl compounds such as α-phenyl-4'-N,N-diphenylaminostylbene, 5-[4-(di-p-tolylamino)benzylidene]-5H-dibenzo[a,d]cycloheptene, etc.; benzidine compounds; triarylmethane compounds; polymers such as poly-N-vinylcarbazole, polyvinylanthracene having in the main chain or a side chain a triphenyl amine or derivative thereof.

Inorganic materials such as selenium, seleniumtellurium, amorphous silicon, etc. may also be used in addition to the organic charge-transporting materials.

The above-mentioned charge-transporting materials may be used singly or in combination of two or more materials.

When a charge-transporting material having no film-forming property is used, a suitable binder may be used with it. Specific examples of the binders include insulative resins such as acrylic resins, polyarylates, polyesters, polycarbonates, polystyrenes, acrylnitrile-styrene copolymers, polysulfones, polyacrylamides, polyamides, chlorinated rubbers, etc.; organic photoconductive polymers such as poly-N-vinylcarbazole, polyvinylanthracene, etc; and the like.

Useful materials for the electroconductive support include aluminum, aluminum alloys, copper, zinc, stainless steel, titanium, etc. In addition thereto, also useful are plastics coated with a film of these metal formed by vacuum vapor deposition; plastic or metal supporters coated with electroconductive particles (e.g., carbon black, silver particles etc.) together with a binder; plastics or paper impregnated with electroconductive particles; and the like.

The electroconductive support may either be in a form of sheet or in a form of a drum.

Between the electroconductive supporter and the photosensitive layer, a subbing layer may be provided which has a barrier function and an adhesion function. The subbing layer may have a thickness of 5 μm or less, preferably from 0.1 μm to 3 μm. The subbing layer may be formed from a material such as casein, polyvinyl alcohol, nitrocellulose, polyamides (nylon 6, nylon 66, nylon 610, copolymer nylon, N-alkoxymethylated nylon, etc), polyurethane, aluminum oxide, etc.

Over the photosensitive layer, there may be laminated a resin layer, or a resin layer containing electroconductive material dispersed therein, as a protecting layer.

Another specific example of the present invention is an electrophotographic photosensitive member containing the above-mentioned compound and a charge transporting material in the same layer. In this example, a charge transfer complex composed of poly-N-vinylcarbazole and trinitrofluorenone may be used as the charge transporting material.

The electrophotographic photosensitive member of this example may be formed by applying a liquid comprising the above-mentioned compound and the charge transporting material dispersed in a suitable resin solution, and drying it.

In any electrophotographic photosensitive member, the employed compound represented by the general formula (1) or (2) may either be crystalline or non-crystalline, and may be employed in combination of two or more compounds represented by the general formula (1) or (2), or in combination with a known charge-generating material.

The electrophotographic photosensitive member of the present invention is useful not only for electrophotographic copying machines but is also widely useful in electrophotography application field such as laser beam printers, CRT printers, LED printers, liquid crystal printers, laser engraving, etc.

FIG. 1 illustrates an outline of constitution of a usual transfer-type electrophotographic photosensitive member employing a photosensitive member in a drum form.

In the figure, the numeral 1 denotes a drum type photosensitive member as an image bearer, which is driven to rotate around the axis 1a in the arrow direction at a predetermined peripheral speed. The photosensitive member 1 is electrostatically charged uniformly to a predetermined positive or negative potential at the peripheral surface with a charging means 2 while rotating. Then it is exposed to an image-projecting light L (e.g., slit projection, laser beam scanning projection, etc.) at the light exposure portion 3 from an image-projecting means not shown in the figure. Thus an electrostatic latent image is successively formed on the periphery surface of the photosensitive member.

The electrostatic latent image is subsequently developed by use of a toner with the image-developing means 4. The developed toner image is sequentially transferred onto the transfer-receiving medium P which is fed between the photosensitive member 1 and the transfer means synchronously with the rotation of the photosensitive member 1 by a transfer means 5 not shown in the figure.

The transfer-receiving medium P having received the transferred image is separated from the photosensitive member surface to be introduced to the image fixing means 8 to have the image fixed and to be output from the machine as a duplicate (a copied material).

After the image transfer, the surface of the photosensitive member 1 is cleaned with a cleaning means 6 to remove the residual toner, and is repeatedly used for image formation.

As the charging means 2 for uniformly charging the photosensitive member 1 electrostatically, corona charging apparatuses are generally and widely used. As the transferring apparatus, corona transferring means are also generally and widely used. Plural means out of the constitutional elements, such as a photosensitive member, a developing means, and a cleaning means, may be integrated into one apparatus unit, which may be made freely mountable and dismountable. For example, the photosensitive member 1 and the cleaning means 6 are integrated into one apparatus unit and are made to be freely mountable and dismountable by use of a guide means such as a rail in the main apparatus. The apparatus unit may be constituted by incorporating a charging means and/or a developing means.

EXAMPLES 1-17

On an aluminum substrate plate, a subbing layer having a dried film thickness of 1 μm was provided by applying with a Meyer bar a solution of 5 g of a methoxymethylated nylon resin (number-average molecular weight: 32,000) and 10 g of an alcohol-soluble copolymer nylon resin (number-average molecular weight: 29,000) in 95 g of methanol.

Separately, 5 g of the Compound 3 shown before was added in a solution of 2 g of a butyral resin (butyralation degree: 63 mole %) in 95 g of cyclohexanone and was dispersed with a sand mill for 20 minutes. This dispersion was applied on the preliminarily formed subbing layer to give a dried thickness of 0.2 μm with a Meyer bar, to form a charge-generating layer.

The hydrazone compound (5 g) represented the formula below as the charge-transporting material,

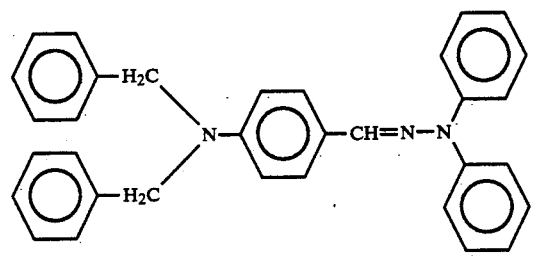

and 5 g of polymethyl methacrylate (number-average molecular weight: 100,000) were dissolved in 40 g of monochlorobenzene. The solution was applied on the charge-generating layer prepared above with a Meyer bar and dried to form a charge-transporting layer having a thickness of 20 μm, thus preparing a photosensitive member of Example 1.

The photosensitive member of Examples 2 to 17 were prepared in the same manner as described above except that compounds other than compound No. 3, which are shown in Table 1, are employed.

The electrophotographic photosensitive members prepared thus were evaluated for charging characteristics by the use of an electrostatic copying paper tester (Model SP-428, made by Kawaguchi Denki K. K.), where the photosensitive member was negatively charged by corona discharge of −5 KV, left standing for 1 second in the dark, and exposed to light of 10 lux with a halogen lamp. The evaluation of the charging characteristics were performed by measuring the surface potentials ($V_0$) and the amounts of exposure ($E_{\frac{1}{2}}$) required for decreasing the surface potential to half of the value after left standing in the dark.

The results are shown in Table 1.

TABLE 1

| Example No. | Compound No. | $V_0 (-V)$ | $E_{\frac{1}{2}}$ (lux · sec) |
|---|---|---|---|
| 1 | 3 | 710 | 3.2 |
| 2 | 4 | 705 | 2.4 |
| 3 | 5 | 710 | 2.9 |
| 4 | 6 | 700 | 1.3 |
| 5 | 7 | 725 | 1.1 |
| 6 | 8 | 715 | 4.5 |
| 7 | 9 | 720 | 3.8 |
| 8 | 10 | 715 | 2.1 |
| 9 | 11 | 710 | 4.1 |
| 10 | 12 | 725 | 3.8 |
| 11 | 13 | 705 | 2.9 |
| 12 | 14 | 720 | 2.1 |
| 13 | 15 | 690 | 2.3 |
| 14 | 16 | 710 | 3.2 |
| 15 | 17 | 705 | 2.8 |
| 16 | 18 | 685 | 6.3 |
| 17 | 19 | 695 | 7.2 |

EXAMPLES 18–22

The electrophotographic photosensitive members prepared in Examples 4, 5, 8, 12, and 13 were charged to −700 V, and the amounts of light exposure ($E_{\frac{1}{2}}$·μJ/cm$^2$) to reduce the potential by half were measured with the apparatus used in Example 1. The light source used was an aluminum/gallium/arsine semiconductor laser (oscillation wavelength: 780 nm). The results are shown in Table 2.

TABLE 2

| Example No. | Compound No. | $E_{\frac{1}{2}}$ (μJ/cm$^2$) |
|---|---|---|
| 18 | 6 | 0.48 |
| 19 | 7 | 0.45 |
| 20 | 10 | 0.62 |
| 21 | 14 | 0.58 |
| 22 | 15 | 0.53 |

These results show that the electrophotographic photosensitive members of the present invention have sufficient sensitivity also in the wavelength region of semiconductor laser oscillation.

EXAMPLES 23–26

The electrophotographic photosensitive member prepared in Example 1 was sticked to a cylinder of an electrophotographic copying machine equipped with a −6.5 KV corona charger, an optical exposing system, an image developer, a transfer charger, a charge-eliminating optical exposing system, and a cleaner.

The dark potential ($V_D$) and the light potential ($V_L$) at the initial stage were set respectively at around −700 V and −200 V. After repetedly used 5000 times, the dark potential and the light potential were measured.

The evaluation was conducted also for the photosensitive members prepared in Examples 4, 5, and 10. The results are shown in Table 3.

TABLE 3

| Example No. | Compound No. | Initial | | After 5000 repetitions | |
|---|---|---|---|---|---|
| | | $V_D(-V)$ | $V_L(-V)$ | $V_D(-V)$ | $V_L(-V)$ |
| 23 | 3 | 700 | 195 | 690 | 220 |
| 24 | 6 | 705 | 200 | 670 | 215 |
| 25 | 7 | 700 | 205 | 660 | 205 |
| 26 | 12 | 700 | 200 | 680 | 210 |

EXAMPLE 27

On a aluminum surface of aluminum-vapor-deposited polyethylene terephthalate film, a subbing layer of polyvinyl alcohol having a film thickness of 0.5 μm was formed. Thereon, the compound dispersion employed in Example 4 was applied with a Meyer bar and dried to form the charge generation layer of 0.2 μm thick.

The styryl compound (5 g) represented by the formula below as the charge-transporting material:

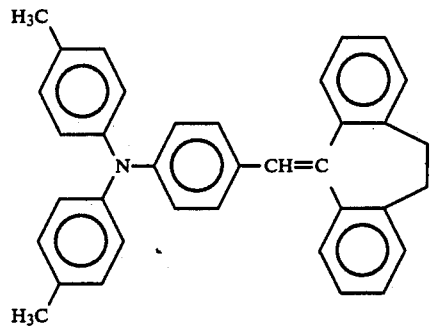

and 5 g of a polycarbonate resin (number-average molecular weight: 55,000) were dissolved in 40 g of tetrahydrofuran. This solution was applied on the charge-generating layer prepared above and dried to form a charge-transporting layer of 20 μm thick. The photosensitive member thus prepared was tested for charging characteristics and durability in the same manner as in Example 1 and Example 23.

The results are shown below. The negative sign for the variation of the potential (ΔV) means the decrease of the absolute value of the potential, and the positive sign means the increase.

| $V_0$: 710 (−V) | $E_{\frac{1}{2}}$: 2.5 (lux · sec) |
|---|---|
| $\Delta V_D$: −10 (V) | $\Delta V_L$: +10 (V) |

EXAMPLE 28

A photosensitive member was prepared by applying the charge-generating layer and the charge-transporting layer of Example 27 in order of the charge-transporting layer and the charge generation layer in this Example. The photosensitive member was evaluated for charging characteristics in the same manner as in Example 1, provided that the charging was made positive.

| $V_0$: 695 (+V) | $E_{\frac{1}{2}}$: 5.3 (lux · sec) |
| --- | --- |

EXAMPLE 29

On the charge transporting layer prepared in Example 1, a solution of 5 g of 2,4,7-trinitro-9-fluorenone and 5 g of poly-4,4'-dioxydiphenyl-2,2'-propane carbonate (molecular weight: 300,000) dissolved in 50 g of tetrahydrofuran was applied with a Meyer bar and dried to form a charge-transporting layer of 18 μm thick.

The electrophotographic photosensitive member prepared thus was evaluated for charging characteristics in the same manner as in Example 1, provided that the charging was made positive.

| $V_0$: 695 (+V) | $E_{\frac{1}{2}}$: 5.7 (lux · sec) |
| --- | --- |

EXAMPLE 30

The Compound No. 6 (0.6 g) was shaken with 9.5 g of cyclohexanone by the use of a paint shaker for 5 hours to disperse the compound. Thereto a solution of 5 g of the charge-transporting material employed in Example 1 and 5 g of a polycarbonate resin dissolved in 40 g of tetrahydrofuran was added, and the mixture was shaken for further 1 hour. The coating liquid thus prepared was applied and dried on an aluminum substrate plate by means of a Meyer bar to form a photosensitive layer of 20 μm thick.

The electrophotographic photosensitive member prepared thus was evaluated for charging characteristics in the same manner as in Example 1, provided that the charging was made positive.

| $V_0$: 695 (+V) | $E_{\frac{1}{2}}$: 5.7 (lux · sec) |
| --- | --- |

We claim:

1. An electrophotographic photosensitive member having a photosensitive layer on an electroconductive support, said photosensitive layer comprising a compound having pi electron conjugation represented by the general formula (1) or (2) having in the molecule thereof an electron-donating portion and an electron-accepting portion:

(1)

(2)

where D is an electron-donating aromatic group or an electron-donating heterocyclic group; A is an electron-accepting aromatic group or an electron-accepting heterocyclic group; B is a hydrogen atom, or an aromatic or heterocyclic group which may form a ring together with A or D; m is an integer of 1, 2, or 3; and n is an integer of 0 or 1.

2. The electrophotographic photosensitive member according to claim 1, wherein B in the general formulas (1) and (2) is a hydrogen atom.

3. The electrophotographic photosensitive member according to claim 1, wherein D in the general formulas (1) and (2) is at least one selected from the group consisting of aromatic monocyclic groups and aromatic condensed polycyclic groups which may have an electron-donating substituent; assembled ring groups constituted by direct combination of two or more of the aromatic monocyclic groups and the aromatic condensed polycyclic groups; aromatic amine groups which may have an electron-donating substituent; heterocyclic monocyclic groups which may have an electron-donating substituent; condensed heterocyclic groups constituted of a heterocyclic group condensed with benzene ring or with an aromatic condensed polycyclic ring; and assembled ring groups constituted by direct combination of two or more of the heterocyclic monocyclic groups and the condensed heterocyclic groups.

4. The electrophotographic photosensitive member according to claim 3, wherein D in the general formulas (1) and (2) is at least one selected from the group consisting of aromatic monocyclic groups and aromatic condensed polycyclic groups which may have an electron-donating substituent; assembled ring groups constituted by direct combination of two or more of the aromatic monocyclic groups and the aromatic condensed polycyclic groups; aromatic amine groups which may have an electron-donating substituent; heterocyclic monocyclic groups which may have an electron-donating substituent; condensed heterocyclic groups constituted of a heterocyclic group condensed with benzene ring or with an aromatic condensed polycyclic ring; and assembled ring groups constituted by direct combination of two or more of the heterocyclic monocyclic groups and the condensed heterocyclic groups through a double bond.

5. The electrophotographic photosensitive member according to claim 3, wherein D in the general formulas (1) and (2) is at least one selected from the group consisting of benzene, naphthalene, anthracene, phenanthrene, indene and fluorene, which have an electron-donating substituent; pyrene which may have an electron-donating substituent; assembled ring groups constituted by direct combination of two or more of said aromatic monocyclic and condensed polycyclic groups; triphenylamine, diphenylamine, and diphenylmethylamine which, may have an electron-donating substituent; furan, thiophene, pyrrole, oxazole, thiazole, imidazole, pyridine, pyrazine, acridine, phenazine, benzofuran, benzothiophene, dibenzofuran, dibenzothiophene, benzoxazole, benzothiazole, thianthrene, phenoxazine, and phenothiazine, which have an electron-donating substituent; indole, carbazole, iminodibenzyl, tetrathiafulvalene, and dibenzotetrathiafulvalene, which may have a substituent; condensed heterocyclic groups constituted of a heterocyclic group condensed with a benzene ring or an aromatic condensed polycyclic group; and assembled ring groups constituted by direct combination of two or more of said monocyclic and condensed polycyclic groups.

6. The electrophotographic photosensitive member according to claim 1, wherein A in the general formulas (1) and (2) is at least one selected from the group consisting of aromatic monocyclic groups and aromatic condensed polycyclic groups which have an electron-accepting substituent; assembled ring groups constituted by direct combination through a double bond of two or more of said aromatic monocyclic and condensed polycyclic groups; aromatic ketone groups which may have an electron-accepting substituent, and dicyanomethylene derivatives thereof; aromatic thioketone groups; and aromatic quinone groups, and dicyanomethylene derivatives thereof; heterocyclic monocyclic groups which have an electron-accepting substituent; condensed heterocyclic groups constituted of the heterocyclic monocyclic group condensed with a benzene ring or an aromatic condensed polycyclic group; and assembled ring groups constituted by direct combination of two or more of said monocyclic and condensed polycyclic groups.

7. The electrophotographic photosensitive member according to claim 6, wherein A in the general formulas (1) and (2) is at least one selected from the group consisting of aromatic ketone groups which may have an electron-accepting substituent, and dicyanomethylene derivatives thereof; aromatic thioketone groups; and aromatic quinone groups and dicyanomethylene derivatives thereof.

8. The electrophotographic photosensitive member according to claim 6, wherein A in the general formulas (1) and (2) is at least one selected from the group consisting of benzene, naphthalene, anthracene, phenanthrene, indene, and fluorene which have an electron-accepting substituent; assembled ring groups constituted by direct combination through a double bond of two or more of said aromatic monocyclic or condensed polycyclic groups; benzophenone, fluorenone, and benzanthrone, which may have an electron-accepting substituent, and dicyanomethylene derivatives thereof; benzoquinone, naphthoquinone, anthraquinone, and pyrenequinone, and dicyanomethylene derivatives thereof; furan, thiophene, pyrrole, oxazole, thiazole, imidazole, pyridine, pyrazine, acridine, phenazine, benzofuran, benzothiophene, dibenzofuran, dibenzothiophene, benzoxazole, benzothiazole, thianthrene, phenoxazine, and phenothiazine, which have an electron-accepting substituent; condensed heterocyclic groups constituted by condensing said group with a benzene ring or an aromatic condensed polycyclic group; and assembled ring groups constituted by direct combination of two or more of said monocyclic and condensed polycyclic groups.

9. The electrophotographic photosensitive member according to claim 1, wherein the photosensitive layer has a lamination structure comprising a charge-generating layer and a charge-transporting layer.

10. The electrophotographic photosensitive member according to claim 9, wherein the charge-generation layer is provided on an electroconductive support, and the charge-transporting layer is provided further on the charge-generation layer.

11. The electrophotographic photosensitive member according to claim 9, wherein the charge-transporting layer is provided on an electroconductive support, and the charge-generation layer is provided further on the charge-transporting layer.

12. The electrophotographic photosensitive member according to claim 1, wherein a subbing layer is provided between the electroconductive support and the photosensitive layer.

13. The electrophotographic photosensitive member according to claim 1, wherein a protective layer is provided on the photosensitive layer.

14. An electrophotographic device comprising an electrophotographic photosensitive member having a photosensitive layer on a electroconductive support, said photosensitive layer contains a compound having pi electron conjugation represented by the general formula (1) or (2) having in the molecule thereof an electron-donating portion and electron-accepting portion:

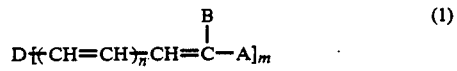

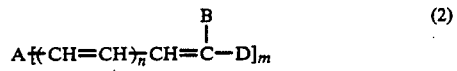

wherein D is an electron donating aromatic group or an electron donating heterocyclic group, A is an electron-accepting aromatic group or an electron-accepting heterocyclic group, B is a hydrogen atom, or an aromatic group or heterocyclic group which may form a ring together with A or D, m is an integer of 1, 2 or 3, and n is an integer of 0 or 1.

* * * * *

UNITED STATES PATENT AND TRADEMARK OFFICE
CERTIFICATE OF CORRECTION

PATENT NO. : 5,034,294

DATED : July 23, 1991

INVENTOR(S) : Shintetsu Go, et al

It is certified that error appears in the above-identified patent and that said Letters Patent is hereby corrected as shown below:

COLUMN 17

Line 23, "$V_0:695(+V) \quad E\frac{1}{2}:5.7(lux \cdot sec)$" should read --$V_0:690(+V) \quad E\frac{1}{2}:5.7(lux \cdot sec)$--.

Signed and Sealed this

Twenty-second Day of December, 1992

Attest:

DOUGLAS B. COMER

*Attesting Officer*     *Acting Commissioner of Patents and Trademarks*